Figure 1:
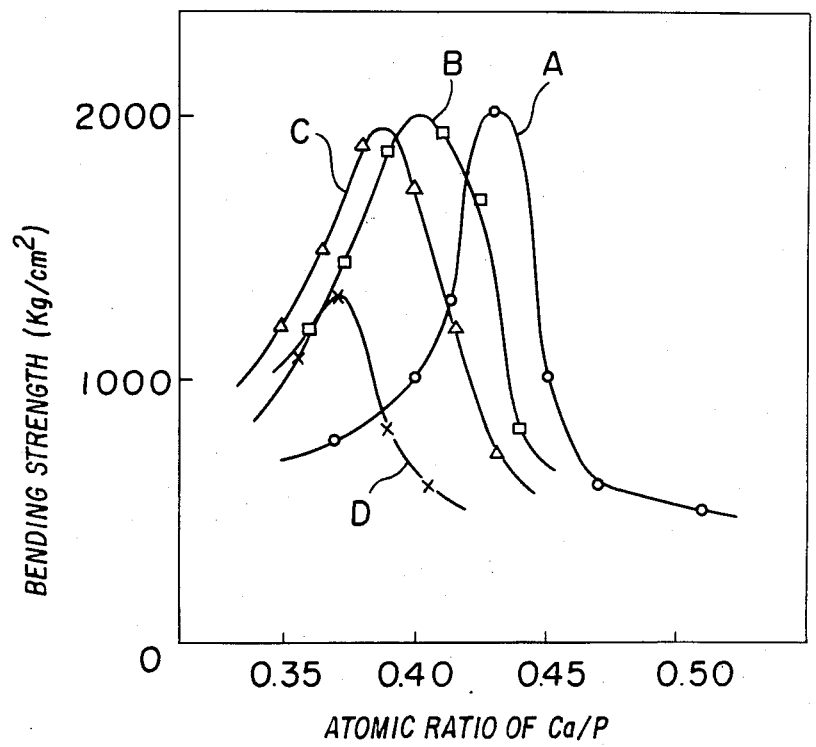

United States Patent [19]

Manabe et al.

[11] Patent Number: 4,617,279

[45] Date of Patent: Oct. 14, 1986

[54] CALCIUM PHOSPHATE TYPE CRYSTALLIZABLE GLASS

[75] Inventors: Tsuneo Manabe, Yokohama; Shigeyoshi Kobayashi, Kawasaki; Hitoshi Kijimuta, Ebina, all of Japan

[73] Assignee: Asahi Glass Company Ltd., Tokyo, Japan

[21] Appl. No.: 775,355

[22] Filed: Sep. 12, 1985

[30] Foreign Application Priority Data

Sep. 14, 1984 [JP] Japan .................................. 59-191437

[51] Int. Cl.[4] .......................... C03C 10/02; C03C 3/17
[52] U.S. Cl. ........................................ 501/10; 501/48; 106/35
[58] Field of Search ..................... 501/10, 48; 106/35

[56] References Cited

U.S. PATENT DOCUMENTS

| | | | |
|---|---|---|---|
| 1,570,202 | 1/1926 | Buck | 501/48 |
| 3,300,670 | 1/1967 | Veres | 501/48 |
| 3,981,736 | 9/1976 | Bruemer et al. | 501/10 |
| 4,026,714 | 5/1977 | Lewis | 501/48 |
| 4,366,253 | 12/1982 | Yagi | 501/64 |

FOREIGN PATENT DOCUMENTS 55-11625  3/1980  Japan ................................. 501/10

OTHER PUBLICATIONS

Wihsmann et al.; "Bioaktive Implantate auf der Basis von Vitrokerammaterialien", Wiss. Ztschr. Friedrich-Schiller Univ. Jena, Math.-Naturwiss. R., 32, Jg (1983), H. 2/3, pp. 553–569.
Kihara, Seijé et al.; "Calcium Phosphate Glass–Ceramic Crown Prepared by Lost-Wax Technique", Communications of the American Ceramic Society, pp. C100–101, Jun. 1984.

Primary Examiner—Mark L. Bell
Attorney, Agent, or Firm—Oblon, Fisher, Spivak, McClelland & Maier

[57] ABSTRACT

Calcium phosphate type crystallizable glass for dental materials, which is composed essentially of from 41 to 49.5 mol % of CaO, from 50 to 58.5 mol % of $P_2O_5$ and from 0.5 to 5 mol % of $Al_2O_3$, and which has an atomic ratio of calcium to phosphorus (Ca/P) within a range of from 0.35 to 0.49.

3 Claims, 1 Drawing Figure

CALCIUM PHOSPHATE TYPE CRYSTALLIZABLE GLASS

The present invention relates to calcium phosphate type crystallizable glass for dental materials, and calcium phosphate type crystallized glass obtained therefrom. More particularly, the present invention relates to calcium phosphate type crystallizable glass, from which highly strong, highly water resistant, translucent crystallized glass having a milky white color or a color and color tone resembling those of natural teeth is obtainable which is suitable for use as dental materials such as artificial teeth, crowns, inlays or bridges.

As dental materials such as artificial teeth, artificial roots of teeth, crowns, inlays or bridges, or as ceramic materials for living bodies such as artificial bones for surgery, there has been proposed, e.g. in Japanese Examined Patent Publication No. 11625/1980, calcium phosphate type crystallized glass having a crystallinity of at least 20%, which is obtained by melting and molding a glass composed of from 28 to 57% by weight of CaO and from 72 to 43% by weight of $P_2O_5$, or such a glass containing at most 10% by weight of $Al_2O_3$, $SiO_2$ or $B_2O_3$, followed by heat treatment.

This calcium phosphate type crystallized glass has a composition similar to that of natural teeth or natural bones, and its physical, chemical and mechanical properties are close to those of natural teeth and natural bones. Thus, it has good compatibility with living bodies. Yet, it can be prepared by a simple process such that a starting material is melted and poured into a mold, like a glass, to obtain a molded product having a desired shape, followed by crystallization. Further, the shrinkage during the process for its preparation is as small as at most 1%, and fine processing is not required even for a complicated configuration. Thus, it is expected to be a prospective material having superior properties and high productivity as compared with the conventional metallic materials or ceramic materials, as dental materials or ceramic materials for living bodies such as bones for surgery.

Further, a process for the production of calcium phosphate type crystallized glass suitable for use as a restorative material, is proposed in Japanese Unexamined Patent Publication No. 141508/1984 or No. 141509/1984, or in "COMMUNICATIONS OF AMERICAN CERAMIC SOCIETY" C-100(1984).

However, such conventional calcium phosphate type crystallized glass had the following practical problems.

(1) Cracks are likely to form during crystallization, and crystallized glass having adequate strength for practical use is hardly obtainable.

(2) A number of pores having a diameter of about 1 μm are present in the glass crystallized structure, and the crystallized glass is white and opaque and thus presents an outer appearance which is different from natural teeth.

(3) The deterioration of the strength in water is substantial, and it is not durable for use in a mouth.

It is an object of the present invention to solve the above-mentioned problems, and to provide calcium phosphate type crystallizable glass for dental materials, from which highly strong, highly water resistant calcium phosphate type crystallized glass having a translucent outer appearance is obtainable.

The present invention provides calcium phosphate type crystallizable glass for dental materials, which is composed essentially of from 41 to 49.5 mol % of CaO, from 50 to 58.5 mol % of $P_2O_5$ and from 0.5 to 5 mol % of $Al_2O_3$, and which has an atomic ratio of calcium to phosphorus (Ca/P) within a range of from 0.35 to 0.49.

The present invention provides also calcium phosphate type crystallized glass prepared by crystallizing the above calcium phosphate type crystallizable glass.

Now, the present invention will be described in detail with reference to the preferred embodiments.

In the accompanying drawing, FIG. 1 is a graph showing the relation between the atomic ratio of Ca/P and the bending strength of the calcium phosphate type crystallized glass obtained by the present invention.

For the purpose of the present invention, the "crystallizable glass" means glass which has not yet been subjected to crystallization treatment, and the "crystallized glass" means glass which has been treated for crystallization.

Calcium phosphate type crystallizable glass to be used in the present invention, is composed of calcium metaphosphate ($CaO \cdot P_2O_5$) having a chain structure whether it is in a vitrified state or in a crystallized state, and should have an atomic ratio of calcium to phosphorus (Ca/P) within a range of from 0.35 to 0.49 so that the glass has a proper melting point and melt viscosity for efficient casting, and the crystallized glass will have adequate strength and water resistance. Namely, the calcium phosphate type crystallizable glass as the base material most suitably has a composition comprising from 41.0 to 49.5 mol % of CaO and from 50.5 to 59.0 mol % of $P_2O_5$.

In the present invention, the water resistance is evaluated primarily on the basis of the outer appearance and bending strength after soaking in distilled water.

If the ratio of Ca/P exceeds 0.49, it is difficult to obtain crystallized glass having adequate bending strength, such being undesirable. On the other hand, if the ratio is lower than 0.35, crystallization hardly takes place, and it becomes difficult to obtain uniformly crystallized glass, and at the same time the phosphorus component becomes excessive, whereby water resistance deteriorates.

Such calcium phosphate type crystallizable glass has a composition similar to that of natural teeth or bones, which are composed mainly of calcium phosphate materials, and which have an atomic ratio of calcium to phosphorus (Ca/P) within a range of from about 1.75 to about 2.0. Thus, it has good affinity with living bodies. With glass having such a composition, it is possible to obtain an artificial dental product having a desired shape by a simple process comprising melting the glass material and pouring it into a mold, followed by crystallization.

In the present invention, $Al_2O_3$ is added to the calcium phosphate type crystallizable glass having the above base composition, in an amount of from 0.5 to 5 mol % relative to the calcium phosphate type crystallizable glass, in order to improve the water resistance of the glass and the crystallized glass. If the amount of $Al_2O_3$ exceeds 5 mol %, the crystallizable glass tends to be brittle, and cracks are likely to form during the crystallization, whereby it is difficult to obtain highly strong crystallized glass. On the other hand, if the amount is less than 0.5 mol %, no adequate effect for the improvement of the water resistance will be obtained.

The calcium phosphate type crystallizable glass containing $Al_2O_3$ according to the present invention has the following composition:

CaO: 41–49.5 mol % (21–28 wt %)
P$_2$O$_5$: 50–58.5 mol % (71–78 wt %)
Al$_2$O$_3$: 0.5–5 mol % (1–5 wt %)

If the CaO content exceeds 49.5 mol % or if the P$_2$O$_5$ content is less than 50 mol %, the proportion of crystals in the crystallized glass tends to be too high when the above-mentioned calcium phosphate type crystallizable glass was crystallized. Consequently, the crystallized glass will be brittle, and cracks are likely to form during the crystallization, whereby it will be difficult to obtain highly strong crystallized glass. Further, a number of pores having a diameter of about 1 μm are likely to form during the crystallization, and the crystallized glass will be white and opaque, such being undesirable. On the other hand, if the CaO content is less than 41 mol %, or if the P$_2$O$_5$ content exceeds 58.5 mol %, crystallization hardly takes place, it will be difficult to obtain crystallized glass having a uniform quality, and the water resistance will be extremely low since the vitrified phase between crystal particles contains P$_2$O$_5$ in a high concentration.

Further, if the Al$_2$O$_3$ content is less than 0.5 mol %, the amount of Al$_2$O$_3$ to chemically stabilize P$_2$O$_5$ in the vetrified phase between crystal particles in the crystallized glass and to prevent the elusion of P$_2$O$_5$ into water, is too small, and the water resistance will be very low. On the other hand, if the Al$_2$O$_3$ content exceeds 5 mol %, the crystallized glass tends to be brittle, and cracks are likely to form during the crystallization, whereby it will be difficult to obtain crystallized glass having high strength.

Within the above-mentioned ranges of the components of the crystallizable glass composition of the present invention, it is particularly preferred to employ the following composition:
CaO: 42–44 mol %
P$_2$O$_5$: 53–55 mol %
Al$_2$O$_3$: 2–4 mol %
and an atomic ratio of calcium to phosphorus (Ca/P) within a range of from 0.38 to 0.42, whereby it will be possible to obtain highly durable crystallized glass having superior bending strength and water resistance.

As raw materials for the production of calcium phosphate type crystallizable glass of the present invention, CaO or a calcium compound capable of being converted to CaO, P$_2$O$_5$ or a phosphorus compound capable of being converted to P$_2$O$_5$ and Al$_2$O$_3$ or an aluminum compound capable of being converted to Al$_2$O$_3$, are mixed and, if necessary, formed into a slurry, then dried and pulverized to obtain calcium phosphate powder containing Al$_2$O$_3$, which is then melted.

For the preparation of a dental product from this calcium phosphate type crystallizable glass, the melt thereby obtained is poured into a mold having a desired shape of the dental material to form a molded product having the desired shape, followed by crystallization to obtain the final product.

As the calcium compound, calcium carbonate and calcium oxide are the most typical representatives. However, other inorganic salts or organic salts of calcium such as calcium hydroxide, calcium hydrogencarbonate, calcium oxalate or calcium acetate, may be also employed.

As the phosphorus compound, there may be mentioned a phosphoric acid such as orthophosphoric acid, or an ammonium phosphate.

Further, a calcium salt of a phosphoric acid such as calcium phosphate, calcium hydrogenphosphate, calcium dihydrogenphosphate, calcium pyrophosphate, calcium polyphosphate or hydroxyapatite, may be used alone or in combination with other calcium compounds or phosphorus compounds.

As the aluminum compound, there may be employed aluminum hydroxide, aluminum oxide or aluminum nitrate.

More specifically, as an example for the preparation of the above-mentioned calcium phosphate type crystallizable glass dental material, from 26 to 34% by weight of finely pulverized CaCO$_3$, from 73 to 66% by weight of H$_3$PO$_4$ and from 0.5 to 5% by weight of Al(OH)$_3$ are thoroughly mixed, water is added thereto to obtain a slurry, the slurry is dried and pulverized to obtain calcium phosphate powder containing an aluminum component, and the powder is baked at a temperature of from 200° to 900° C. for 1 to 10 hours to obtain a glass material. Then, a necessary amount of this glass material is put in a platinum crucible and heated and melted at a temperature of from 900° to 1500° C. for from 5 minutes to 10 hours to obtain a uniformly vitrified glass. An investment mold is preliminarily made by the lost-wax method. That is, a wax pattern having desired shape is sprued and invested and, after the investment has set, the investment mold is heated to remove the wax pattern by burning and then maintained at a temperature of from 500° to 800° C.

The melt of calcium phosphate type crystallizable glass thus obtained is cast and molded in that investment mold. The molded product is then taken out together with the embedding material or from the embedding material, and subjected to crystallization treatment to obtain a final product.

There is no particular restriction in the manner for crystallizing the molded glass product. For instance, it is possible to employ a method wherein the molded product is held in an atmosphere of from 500° to 900° C. for from 5 minutes to 100 hours. By such crystallizing treatment, it is possible to obtain calcium phosphate type crystallized glass having a crystallinity of at least 20%.

In addition to Al$_2$O$_3$, a certain amount of other additives may be incorporated.

Further, in the present invention, from 0.001 to 1 mol % (from 0.001 to 1% by weight) of at least one element selected from the group consisting of Ru, Rh and Pd may be incorporated to impart the color as well as the color tone resembling natural teeth. Ru, Rh or Pd may be incorporated in the molten glass material in the form of elemental metal, an oxide, a hydroxide, a halide, a sulfide, a nitrate, a sulfate or an organic salt.

Now, the present invention will be described in further detail with reference to Examples. However, it should be understood that the present invention is by no means restricted to these specific Examples.

EXAMPLE 1

CaCO$_3$ powder corresponding to 46 mol % (25% by weight) of CaO was mixed with Al(OH)$_3$ powder corresponding to 1 mol % (1% by weight) of Al$_2$O$_3$. To this mixture, phosphoric acid containing H$_3$PO$_4$ corresponding to 53 mol % (74% by weight) of P$_2$O$_5$ was dropwise added. The reaction product thereby obtained was dried and pulverized. The powder thereby obtained was baked at 400° C. for 5 hours. The baked product was melted in a platinum crucible at a temperature of 1250° C. under stirring for 2 hours, and then poured on a graphite plate and gradually cooled.

Calcium phosphate type crystallizable glass having a Ca/P ratio of 0.43 thus obtained, was milled into a rod having a square cross section of 2×2 mm and a length of 50 mm, and the rod was treated at 630° C. for 20 hours for crystallization. With respect to the crystallized glass thereby obtained, the properties such as the bending strength, etc. were measured. The results are shown in Table 1.

1 to obtain calcium phosphate type crystallizable glass. The glass was subjected to crystallizing treatment at 650° C. for 20 hours. The properties of the crystallized glass having an atomic ratio of Ca/P of 0.44 thereby obtained, are shown in Table 1.

TABLE 1

|  | Example 1 | Example 2 | Comparative Example 1 | Comparative Example 2 |
| --- | --- | --- | --- | --- |
| Vickers hardness | 390 | 400 | 380 | 380 |
| Compressive strength (kg/cm$^2$) | 5800 | 6200 | 3900 | 3700 |
| Bending strength (kg/cm$^2$) | 1580 | 1430 | 580 | 870 |
| Density (g/cm$^3$) | 2.8 | 2.8 | 2.7 | 2.7 |
| Bending strength after soaking in distilled water at 37° C. for one week (kg/cm$^2$) | 1430 | 1400 | 380 | 160 |
| Outer appearance | Translucency resembling natural teeth | | Opaque | Opaque |

EXAMPLE 2

$CaH_4(PO_4)_2 \cdot H_2O$ powder corresponding to 45 mol % (25% by weight) of CaO was mixed with $Al(OH)_3$ powder corresponding to 2 mol % (2% by weight) of $Al_2O_3$. To the mixture, phosphoric acid containing $H_3PO_4$ corresponding to 8 mol % (11% by weight) of $P_2O_5$, was dropwise added. The reaction product thereby obtained was dried and melted in a platinum crucible at a temperature of 1250° C. under stirring for 2 hours, and then poured onto an iron plate and gradually cooled to obtain a glass block.

A necessary amount of calcium phosphate type glass having an atomic ratio of Ca/P of 0.425 was cut out from the glass block, and melted in a platinum crucible at 1200° C. Then, the melt was cast and molded in an investment mold preliminarily prepared by a lost-wax method by the use of phosphate bonded investment to have a desired shape and then maintained at a temperature of 600° C., by a centrifugal casting method. The molded product was maintained together with the embedding material at a temperature of 650° C. for 10 hours for crystallizing treatment, whereby a cast crown made of crystallized glass was obtained. The properties of the crystallized glass thus obtained are shown in Table 1.

COMPARATIVE EXAMPLE 1

$CaCO_3$, $Al(OH)_3$ and $H_3PO_4$ were mixed in such amounts that correspond to 52 mol % (30% by weight) of CaO, 1 mol % (1% by weight) of $Al_2O_3$ and 47 mol % (69% by weight) of $P_2O_5$, respectively. The mixture was treated in the same manner as in Example 1 to obtain calcium phosphate type crystallizable glass. This glass was subjected to crystallizing treatment at 630° C. for 20 hours. The properties of the crystallized glass having an atomic ratio of Ca/P of 0.55 thus obtained, are shown in Table 1.

COMPARATIVE EXAMPLE 2

$CaCO_3$ and $H_3PO_4$ were mixed in such amounts that correspond to 47 mol % (26% by weight) of CaO and 53 mol % (74% by weight) of $P_2O_5$, respectively. The mixture was treated in the same manner as in Example 1 to obtain calcium phosphate type crystallizable glass. The glass was subjected to crystallizing treatment at 650° C. for 20 hours. The properties of the crystallized glass having an atomic ratio of Ca/P of 0.44 thereby obtained, are shown in Table 1.

EXAMPLE 3

In the same manner as in Example 1, samples of calcium phosphate type crystallized glass having a composition as identified in Table 2, were prepared. With respect to these samples, the bending strength was measured. The relation between the Ca/P ratio and the bending strength of these glass samples was presented in the graph of FIG. 1.

The data of samples 1a to 1g were plotted to form curve A, the data of samples 2a to 2f were plotted to form curve B, the data of samples 3a to 3f were plotted to form curve C, and the data of samples 4a to 4d were plotted to form curve D, in FIG. 1.

These samples were found to have adequate bending strength and high water resistance.

TABLE 2

| Sample No. | CaO (mol %) | $P_2O_5$ (mol %) | $Al_2O_3$ (mol %) | Ca/P (Atomic ratio) |
| --- | --- | --- | --- | --- |
| 1-a | 42 | 57 | 1 | 0.37 |
| 1-b | 44 | 55 | 1 | 0.40 |
| 1-c | 45 | 54 | 1 | 0.42 |
| 1-d | 46 | 53 | 1 | 0.43 |
| 1-e | 47 | 52 | 1 | 0.45 |
| 1-f | 48 | 51 | 1 | 0.47 |
| 1-g | 50 | 49 | 1 | 0.51 |
| 2-a | 41 | 57 | 2 | 0.36 |
| 2-b | 42 | 56 | 2 | 0.38 |
| 2-c | 43 | 55 | 2 | 0.39 |
| 2-d | 44 | 54 | 2 | 0.41 |
| 2-e | 45 | 53 | 2 | 0.42 |
| 2-f | 46 | 52 | 2 | 0.44 |
| 3-a | 40 | 57 | 3 | 0.35 |
| 3-b | 41 | 56 | 3 | 0.37 |
| 3-c | 42 | 55 | 3 | 0.38 |
| 3-d | 43 | 54 | 3 | 0.40 |
| 3-e | 44 | 53 | 3 | 0.42 |
| 3-f | 45 | 52 | 3 | 0.43 |
| 4-a | 40 | 56 | 4 | 0.36 |
| 4-b | 41 | 55 | 4 | 0.37 |
| 4-c | 42 | 54 | 4 | 0.39 |
| 4-d | 43 | 53 | 4 | 0.41 |

EXAMPLE 4

In the same manner as in Example 1, samples of calcium phosphate type crystallized glass having a composition as identified in Table 3, were prepared. With respect to these samples, the bending strength was measured. The results are shown in Table 3.

TABLE 3

| Sample No. | CaO (mol %) | P$_2$O$_5$ (mol %) | Al$_2$O$_3$ (mol %) | Ca/P (Atomic ratio) | Bending strength (kg/cm$^2$) | Bending strength after soaking in distilled water at 37° C. for 1 month (kg/cm$^2$) | Bending strength after soaking in distilled water at 80° C. for 2 days (kg/cm$^2$) | Bending strength after soaking in distilled water at 80° C. for 20 days (kg/cm$^2$) | Outer appearance after soaking in distilled water at 80° C. for 20 days* |
| --- | --- | --- | --- | --- | --- | --- | --- | --- | --- |
| E (Comparative example) | 47 | 53 | 0 | 0.43 | 800 | <100 | <100 | Collapsed during soaking | Collapsed material was white and opaque |
| F (Example) | 46 | 53 | 1 | 0.43 | 2010 | 1430 | 850 | <100 | White and opaque |
| G (Example) | 44 | 54 | 2 | 0.41 | 1920 | 1850 | 1620 | 650 | Slightly opaque only at the surface |
| H (Example) | 43 | 54 | 3 | 0.40 | 1730 | 1710 | 1720 | 1710 | No change |
| J (Example) | 41 | 55 | 4 | 0.37 | 1320 | 1300 | 1230 | 850 | No change |
| K (Example) | 40 | 55 | 5 | 0.36 | 850 | 850 | 630 | 310 | Partially opaque |

*Prior to soaking, Samples E to K were all translucent.

EXAMPLE 5

Crystallized glass was prepared from Sample H (Table 3) glass in Example 4 in the same manner as in Example 1 except that a part of P$_2$O$_5$ was replaced by the substance identified in Table 4.

The crystallized glass thereby obtained had the same properties as Sample H in Example 4, and had the gloss, color and color tone resembling natural teeth.

TABLE 4

| Sample No. | Substance |
| --- | --- |
| L | RuO$_2$ powder corresponding to 0.08% by weight of Ru |
| M | Rh$_2$O$_3$ powder corresponding to 0.02% by weight of Rh |
| N | PdO powder corresponding to 0.04% by weight of Pd |
| S | Mixture of Ru(OH)$_3$ powder corresponding to 0.05% by weight of Ru and PdCl$_3$ powder corresponding to 0.02% by weight of Pd |
| T | Mixture of RuO$_2$ powder corresponding to 0.05% by weight of Ru, Rh$_2$O$_3$ powder corresponding to 0.01% by weight of Rh and PdO powder corresponding to 0.01% by weight of Pd |

As is evident from the Examples, the Comparative Examples, Tables 1 and 3 and FIG. 1, the calcium phosphate type crystallized glass obtained by crystallizing calcium phosphate type crystallizable glass containing from 0.5 to 5 mol % of Al$_2$O$_3$ and having an atomic ratio of Ca/P of from 0.35 to 0.49 has high strength and excellent water resistance with high strength after the soaking test in water, as compared with the calcium phosphate crystallized glass containing from 0.5 to 5 mol % of Al$_2$O$_3$ and having an atomic ratio of Ca/P of from 0.5 to 1.7. Besides, the crystallized glass obtained by the present invention has translucency resembling natural teeth, and its color is milky white or close to the color of natural teeth. Furthermore, the molten glass can readily be molded into a product having a complicated shape by casting method such as a lost-wax method. Thus, the calcium phosphate type crystallizable glass of the present invention is most suitable for artificial dental materials such as artificial teeth, crowns, inlays or bridges.

We claim:

1. Calcium phosphate crystallized glass for dental materials consisting essentially of from 41 to 49.5 mol % of CaO, from 50 to 58.5 mol % of P$_2$O$_5$ and from 0.5 and 5 mol % of Al$_2$O$_3$, and which has an atomic ratio of calcium to phosphorus (Ca/P) of from 0.35 to 0.45.

2. The calcium phosphate crystallized glass according to claim 1, wherein the calcium phosphate crystallized glass is composed essentially of from 42 to 44 mol % of CaO, from 53 to 55 mol % of P$_2$O$_5$ and from 2 to 4 mol % of Al$_2$O$_3$, and has an atomic ratio of calcium to phosphorus (Ca/P) within a range of from 0.38 to 0.42.

3. The calcium phosphate crystallized glass according to claim 1, which further contains from 0.001 to 1 mol % of at least one element selected from the group consisting of Ru, Rh and Pd.

* * * * *